US006891489B2

United States Patent
Turner

(10) Patent No.: US 6,891,489 B2
(45) Date of Patent: May 10, 2005

(54) CROSS-TALK LINEARITY CONNECTION

(75) Inventor: Andrew James Turner, Bucks (GB)

(73) Assignee: PerkinElmer International CV (CH)

( * ) Notice: Subject to any disclaimer, the term of this patent is extended or adjusted under 35 U.S.C. 154(b) by 31 days.

(21) Appl. No.: 10/223,537

(22) Filed: Aug. 19, 2002

(65) Prior Publication Data
US 2003/0080884 A1 May 1, 2003

(30) Foreign Application Priority Data

Aug. 17, 2001 (EP) .............................................. 01307002

(51) Int. Cl.[7] .............................................. H03M 1/12
(52) U.S. Cl. ....................... 341/155; 341/137; 341/116; 345/84; 345/89
(58) Field of Search ................................ 341/155, 137, 341/116, 84, 89

(56) References Cited

U.S. PATENT DOCUMENTS 6,281,820 B1 * 8/2001 Fields ......................... 341/137
6,466,145 B2 * 10/2002 Fields ......................... 341/137

* cited by examiner

Primary Examiner—Michael Tokar
Assistant Examiner—Lam T. Mai
(74) Attorney, Agent, or Firm—St. Onge Steward Johnston & Reens LLC

(57) ABSTRACT

A circuit for processing the outputs of an array of photoconductive detectors, includes amplifiers (101) for amplifying the detector outputs and analogue-to-digital converters (109) for digitizing the amplified outputs. The A to D converters oversample the detector signals. A digital processor (110) then applies a linearity correction to the digitized signals. The circuit is particularly suitable for processing the signals from an array of photoconductive detectors in an FT-IR microscope.

29 Claims, 4 Drawing Sheets

CROSS-TALK LINEARITY CONNECTION

This invention relates to the processing of signals produced from an array of photoconductive detectors. The invention has particular application in the field of FT-IR microscopy.

FT-IR microscopes are used to analyse small samples of material. The microscope has a viewing configuration and a measurement configuration. In both configurations the microscope can be used either in a transmitting mode or a reflecting mode, depending upon the nature of the sample. Typically such a microscope is used in conjunction with an IR spectrophotometer. A microscope of this type generally includes a source of visible radiation and can receive analysing infrared radiation from a source in the spectrophotometer. A typical microscope includes a sample stage for carrying a sample to be investigated and optical elements for guiding radiation from one or other radiation sources to the sample stage. These elements can include a plane mirror, a toroid coupling optic and a Cassegrain mirror assembly acting as a condenser. A microscope also includes a Cassegrain mirror assembly which images the sample at a given magnification at an intermediate image plane from where the radiation is directed to an infrared detector. The microscope also includes an optical microscope which enables an image sample on the stage to be viewed optically by means of visible radiation and thereby enables areas of interest to be identified. The microscope can also include a video camera which can be used in conjunction with the optical microscope in order to create an image of the sample for display on display means of a computer which is used to control the microscope.

Modern microscopes of this type have a stage which can be moved under computer control to allow several areas of interest to be identified, their coordinates stored and data collected subsequently automatically on the basis of that stored data. Such microscopes also include a variable aperture which can be computer controlled and is located at the intermediate image plane to mask off a portion of the sample. This combined with an oversized single detector element enables the measurement of the infrared spectrum of selected areas of the sample. By stepping the stage and repeating the measurement, the system can slowly build-up a digital image of the sample pixel-by-pixel. An arrangement of this type is described in EP-A-0731371. Typically such microscopes employ a liquid nitrogen cooled, photoconductive mercury cadmium telluride MCT element as the infrared detector. A microscope with a single detector has relatively long measurement times and it can take of the order of 10 hours to acquire a 128×128 pixel image.

In order to reduce measurement times, microscopes have been designed which incorporate large detector arrays rather than single detector elements. One known arrangement used in an integrated array of 64×64 liquid nitrogen cooled photovoltaic MCT detectors, each having an area of 60 microns square. These arrangements have however turned out to be very expensive partly because of the increased cost of the detector itself and partly due to the fact that the slow read-out of the multiplexed detector necessitates the use of a sophisticated spectrometer technology called step scan.

We have proposed in European Patent Application No 00307372.3 to use a relatively small detector array whose outputs are sufficiently small in number that they can be processed without the need for complex multiplexing of the outputs. Typically the detector array has 16 detector elements.

The present invention is concerned with a circuit which can be used to process the outputs of such an array.

According to the present invention there is provided a circuit for processing the outputs of an array of photoconductive detectors comprising amplifier means for amplifying the outputs of the detectors, analogue-to-digital conversion means for digitising the amplified outputs and processing means for processing the digitised signals, said processing means being arranged to apply a linearity correction to the digital signals.

Each detector may be operated in a constant voltage mode. Each amplifying means may include a preamplifier associated with each detector and the amplifier outputs may be combined to provide a common positive feedback.

The analogue-to-digital conversion means may be arranged to operate by oversampling the amplified outputs.

The analogue-to-digital conversion means may be arranged to sample optical path difference intervals corresponding to half a laser fringe.

The processing means may be arranged to apply a linearity correction according to the following algorithm $$y'=y/(1-\alpha y)$$

where y is the output of the analogue-to-digital converter y' is the corrected output α is a parameter.

The parameter α may be a constant or it may be a function of energy incident on the detectors. Different elements in the array may require different values of the parameter α.

The invention will be described now by way of example only, with particular reference to the accompanying drawings. In the drawings.

Figure 1:
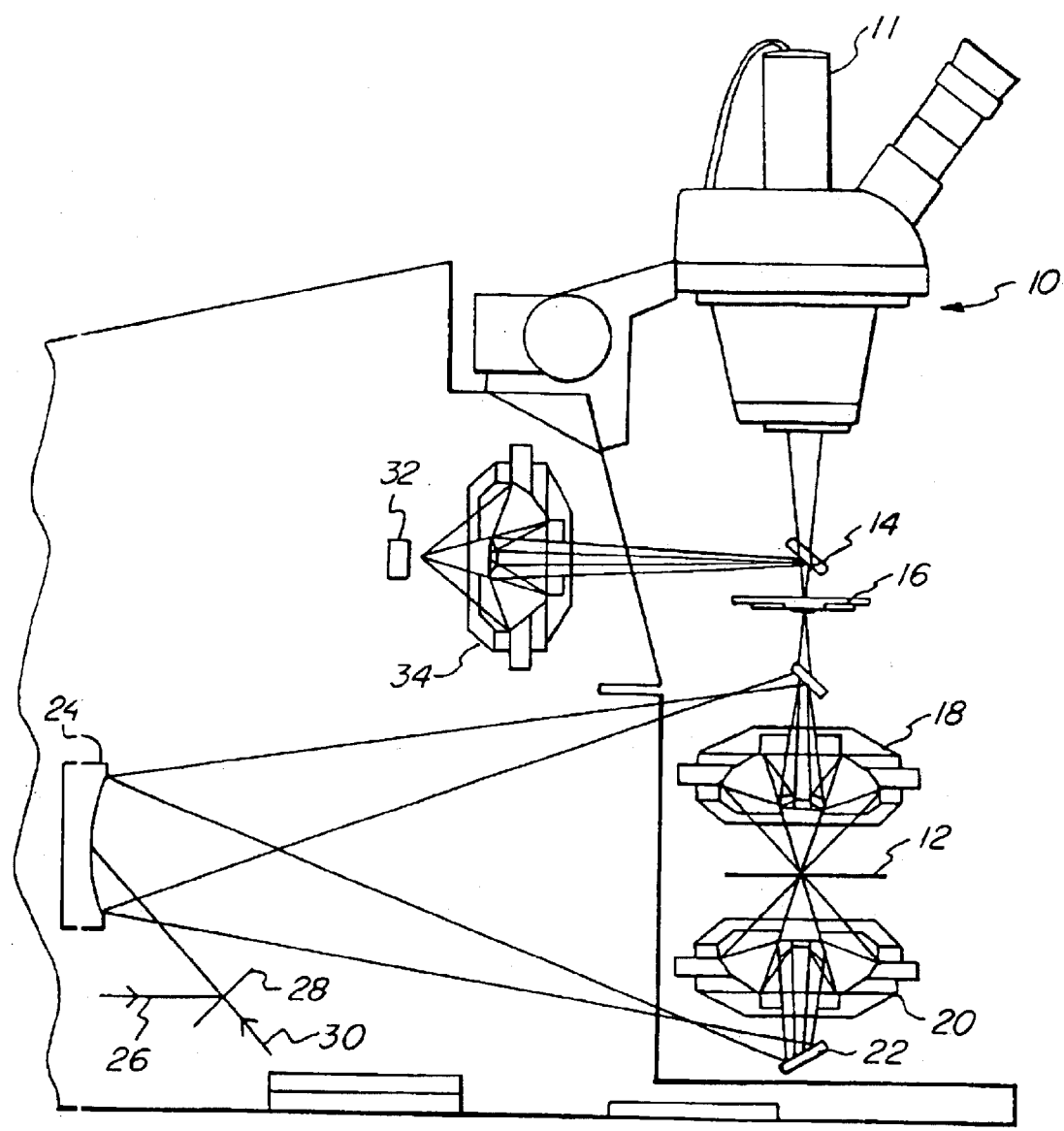
FIG. 1 is a side schematic view of an FT-IR microscope with which the present invention can be used.

Referring to FIG. 1 there are shown the principal elements of an FT-IR microscope with which the present invention can be used. This microscope includes an optical microscope (10) which can be used to view a sample on a sample stage (12) through a dichroic mirror (14), a remote aperture (16) and an objective Cassegrain mirror assembly (18). The optical microscope can incorporate a video camera (11) which is coupled to a computer which controls the microscope. The video camera (11) can be used to create on the display device of the computer a video image of a sample under investigation. The microscope also includes a condenser Cassegrain mirror assembly (20), a lower mirror (22) and a toroid reflector (24). The microscope can receive radiation from a source of infrared radiation (not shown) which may be located in an associated spectrophotometer. The incoming infrared beam (26) is directed by way of a flat dichroic mirror (28) towards the toroid reflector (24). The microscope includes a source of visible radiation (not shown) which can produce a beam (30) of visible radiation along a path which extends through the flat mirror (28). The visible radiation source can be mounted at a suitable location in the microscope.

A detector of infrared radiation such as an MCT detector (32) is disposed laterally from the dichroic mirror (14) and can receive infrared radiation reflected from that mirror by way of a detector Cassegrain mirror assembly (34). The way in which a microscope of this general form operates will be apparent to those skilled in the art and a description can be found for example in an article by D. W. Schiering, E. G. Young and T. P. Byron entitled "An FTIR microscope" published in American Laboratory, November 1990.

In microscopes of the present type the stage (12) is usually movable under computer control in at least a horizontal plane so that areas of interest of a sample located on the stage (12) can be identified using a video image generated by the video camera (11) and data relating to those locations is stored in the computer. The computer then subsequently controls movement of the stage automatically to obtain measurements from the identified areas of the sample. A detailed description of a microscope incorporating this facility can be found in EP-A-0731371.

Figure 2:
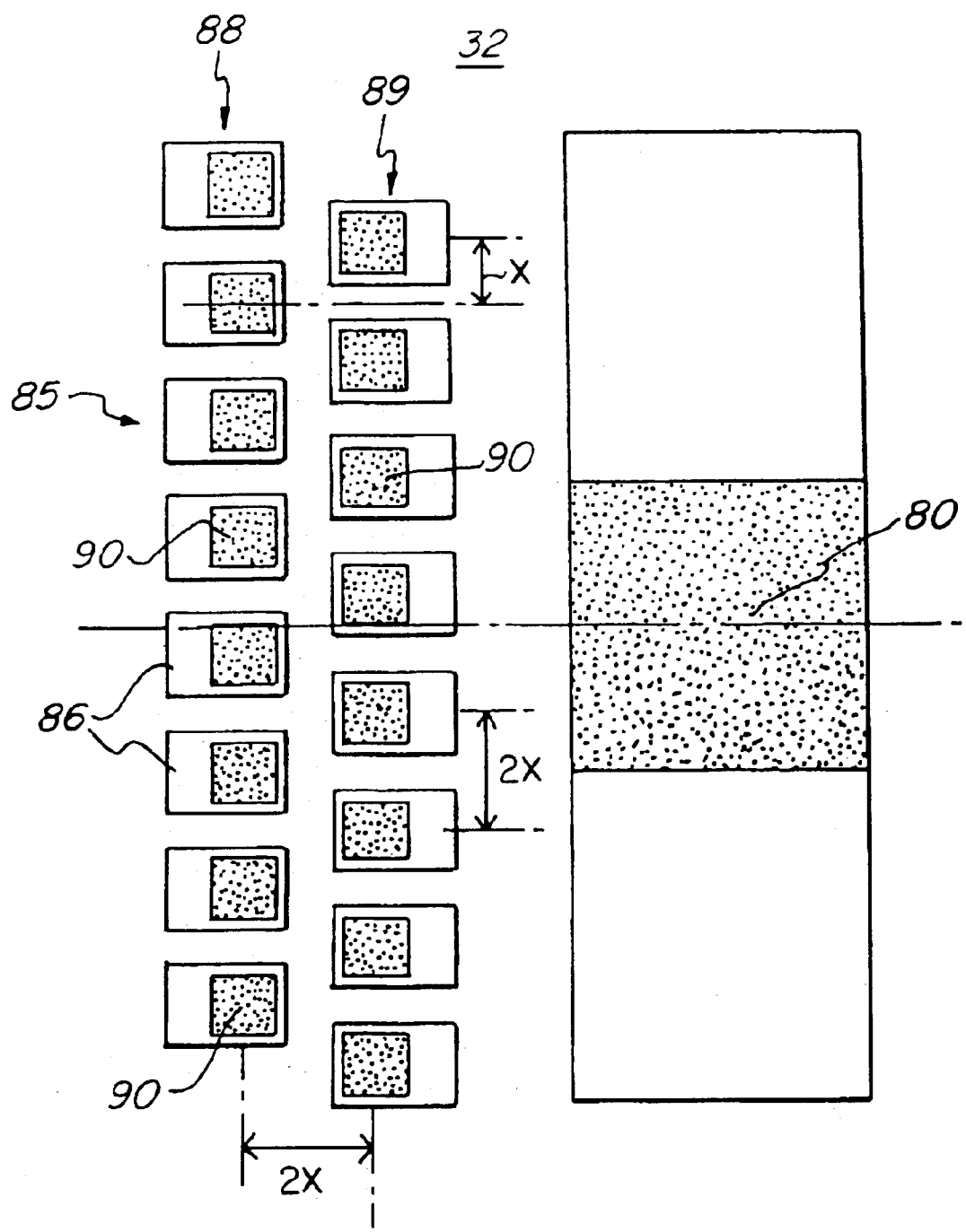
FIG. 2 is a schematic illustration of the structure of the detector used in the microscope of FIG. 1.

Referring now to FIG. 2 of the drawings there is shown schematically a preferred form of detector assembly for use as the detector (32) in the arrangement of FIG. 1. The detector assembly essentially comprises two parts, a first of which is a single detector element (80) of the type which has been used conventionally. The second part comprises a small detector array shown generally at (85). The array comprises sixteen detector elements (86) which are arranged in two rows (88 and 89). Each detector element (86) has a rectangular active area (90) which is responsive to infrared radiation incident on it.

Each of the optically active regions (90) has an output line (not shown) which extends to processing circuitry for processing electrical signals generated by the detector elements (86) when infrared radiation falls thereon. With the arrangement shown in FIG. 2 the signals transmitted along these lines do not require to be multiplexed so that each detector element (86) has its own associated detection circuitry. The detector elements may share a common electrical connection.

The arrangement shown in FIG. 2 of the drawings uses 16 detector elements, i.e. 16 pixels It will be appreciated that other numbers of detector elements can be employed, but 16 has been selected since it is a number which can be achieved economically without having to provide multiplexing. It is envisaged that a range of from 3 to 100 detector elements (86) could be used in the small array.

It will also be appreciated that various alternative configurations of detector elements (86) could be used and not only the one shown in FIG. 2.

Figure 3:
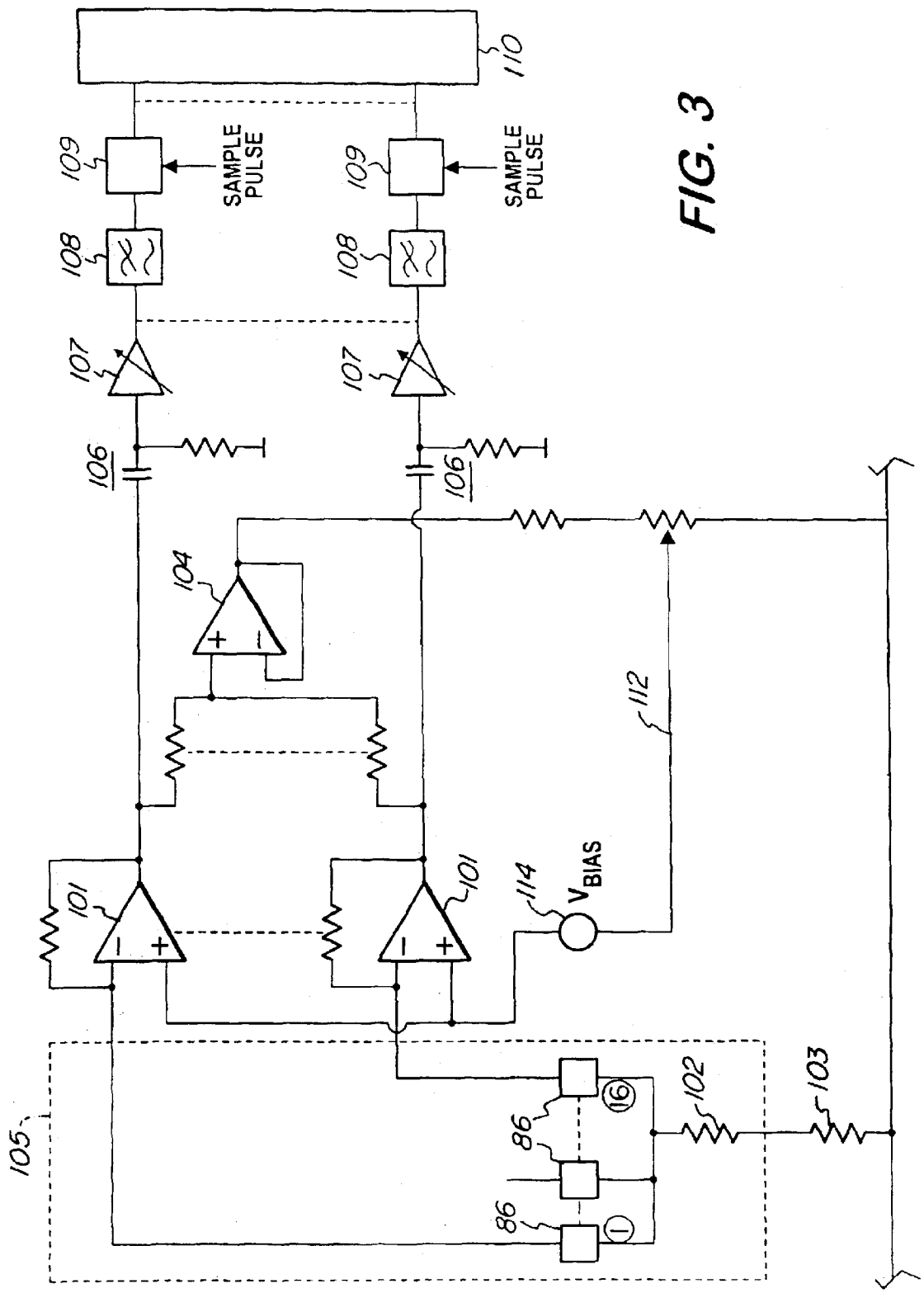
FIG. 3 is a schematic diagram of a circuit which can be used to process the outputs of the detector array shown in FIG. 2.

Circuitry in accordance with an embodiment of the present invention which can be used to process the output signals of the detector elements (86) is shown in FIG. 3 of the drawings. As can be seen from this Figure each detector element is connected to one input of a preamplifier (101). The detectors have a common lead resistance, part of which (102) is internal to the Dewar vessel (105) which contains the detectors and part of which (103) is external. The outputs of the preamplifiers are summed at a summation stage (104) and provide a positive feedback loop to the other input terminal of each preamplifier.

The outputs from the preamplifiers (101) are also fed by way of a DC blocking stage (106) to a variable gain amplifying stage (107). The outputs of the variable gain amplifiers are fed via a low pass filter (108) to analogue-to-digital converters (ADCs) (109) and the outputs of the analogue-to-digital converters (109) are processed a digital signal processor (110). The circuit can be operated without the DC blocking stages (106), but the dynamic range of the signal at the ADCs (109) may be increased significantly.

In the arrangements shown in FIG. 3 each detector (86) operates in a constant voltage mode in conjunction with its linear preamplifier (101). This method is generally used because it is more linear than operating the detector in a constant current mode. However, one consequence of operating in the constant voltage mode is that crosstalk can occur between the detector elements, due to the effects of common lead resistance. In the circuit shown in FIG. 3 crosstalk is reduced by summing the signal from the sixteen preamplifiers at the summation stage (104) and feeding back a fraction of this signal to the bias voltage as positive feedback (112). This compensates for the signal dependent voltage drop across the common lead resistance (102, 103). It will be noted that in the circuit of FIG. 3 there is a common bias voltage (114) and a single positive feedback term for all sixteen detector elements and therefore this arrangement can provide compensation only for the effects of the common lead resistance and cannot correct for other sources of non-linearity in the individual detector elements. The purpose of the positive feedback is therefore principally to provide cancellation of crosstalk. However in doing so it does reduce to a certain extent overall detector non-linearity by eliminating that which would otherwise arise from the common lead resistance.

The outputs from the preamplifiers are fed to the DC blocking filters (106). Ideally the time constant of the DC blocking filter should be long in order to avoid distorting the interferogram. However, mechanical movement of the sample in the microscope can result in large changes in DC level from the detector and this necessitates the use of a short time constant for the DC blocking filter (106) in order for the DC level to settle quickly. Thus, the circuit shown in FIG. 3 uses a short time constant DC blocking filter and the effects of this are compensated by a digital infinite impulse response filter in the digital signal processor (110).

The amplified signals from the variable amplifying stages (107) are digitised by ADCs (109). Each ADC (109) digitises at a rate which involves oversampling of the data. Linearisation is provided in the digital signal processor (110) and the data rate can be subsequently reduced by a technique such as that described in U.S. Pat. No. 5,914,780, or by simple digital filtering depending upon the sampling method used.

Figure 4:
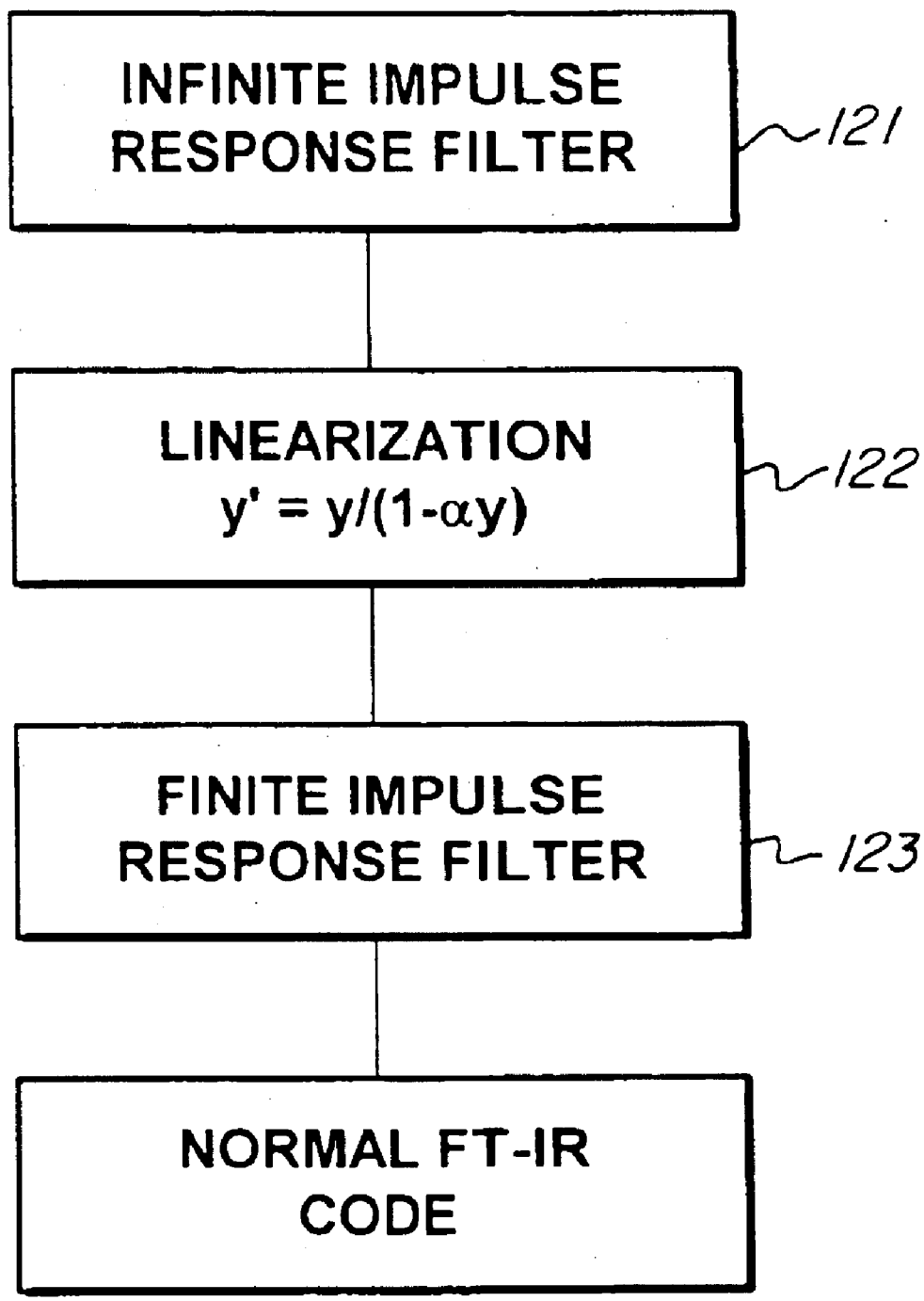
FIG. 4 is a flowchart illustrating the software functions implemented in the digital signal processor of FIG. 3.

The digital signal processor (110) is arranged to perform under software control the functions shown in the flowchart of FIG. 4. The received signals are first applied to an infinite impulse response filter (121), the function of which is described above.

The filtered signals are then subjected to linearisation (122). The algorithm used for linearisation is $y'=y/(1-\alpha y)$ where y is the data from the ADC y' is the value after correction $\alpha$ is a parameter, which may be a constant or may be a function of the time averaged incident energy.

This algorithm is one which will cancel out the effects of non-linearity equivalent to that arising from the fixed series resistance of each detector.

Problems can occur if the bandwidth is limited prior to the linearity stage. This is because the distortion introduced by the detector non-linearity results in harmonics which are required in order to recreate the original illumination signal. Oversampling at the ADC (109) allows the signal bandwidth to be increased, thereby ensuring that these harmonics are not lost whilst not degrading the system signal-to-noise performance.

One form of oversampling at a fixed rate is described in U.S. Pat. No. 5,914,780. Another more conventional way to carry this out is to trigger each ADC (109) at optical path difference intervals corresponding to half a laser fringe. This is equivalent to oversampling by a factor of about 3. In this case a low pass analogue filter is required to limit noise, but the bandwidth can be set to match the oversampling rate and the signal-to noise performance is not significantly degraded.

The linearity correction algorithm can be implemented in software as a binominal expansion of the above equation expressed as follows:

$$y'=y+\alpha y^2+\alpha^2 y^3+\alpha^3 y^4+\alpha^4 y^5 \ldots$$

This is suitable for situations where the processor (110) does not have a fast divide. A five term expansion is generally sufficient for applications involving FT-IR.

After linearity correction a lowpass finite impulse response digital filter (123) reduces the data rate by a factor typically of 2.

The level of positive feedback (112) can be set as a single operation when the system is installed or recalibrated, in order to minimise observed electrical crosstalk between elements. The gain setting for the variable amplifier stages (107) can also be set as a single operation when the system is installed or recalibrated, in order to match the maximum signal levels to the ADCs (109).

The parameter α can be determined by adjusting it to minimise the apparent signal in a single beam spectra below the detector cutoff wavelength. This can be a single operation carried out when a system is installed, although it can also be repeated as part of an ongoing system calibration.

What is claimed is:

1. A circuit for processing the outputs of an array of photoconductive detectors, the circuit comprising: amplifying means for amplifying the outputs of the detectors, analogue-to-digital conversion means for digitizing the amplified outputs and processing means for processing the digitized signals, said processing means being arranged to apply a linearity correction to the digital signals and each amplifying means including a pre-amplifier associated with each detector, the amplifier outputs being combined to provide positive feedback to minimize crosstalk.

2. A circuit according to claim 1, wherein each detector is operated in a constant voltage made.

3. A circuit according to claim 1, wherein the analogue-to-digital conversion means is arranged to operate by oversampling the amplified outputs.

4. A circuit according to claim 3, wherein the analogue-to-digital conversion means is arranged to sample optical path difference intervals corresponding to half a laser fringe.

5. A circuit according to claim 1, wherein the processing means is arranged to apply a linearity correction according to the following algorithm $$y'=y/(1-\alpha y)$$

where y is the output of the analogue-to-digital converter, y' is the corrected output, and α is a parameter.

6. A circuit according to claim 5, wherein the parameter α is a constant.

7. A circuit according to claim 5, wherein the parameter α is a function of energy incident on the detectors.

8. An infrared microscope comprising a circuit having amplifying means for amplifying the outputs of a detector, analogue-to-digital conversion means for digitizing the amplified outputs and processing means for processing the digitized signals, said processing means being arranged to apply a linearity correction to the digital signals, and each amplifying means including a pre-amplifier associated with each detector, the amplifier outputs being combined to provide positive feedback to minimize crosstalk.

9. A circuit for processing the outputs of an array of photoconductive detectors, the circuit comprising:
amplifying means for amplifying the outputs of the detectors;
analogue-to-digital conversion means for digitizing the amplified outputs; and
processing means for processing the digitized signals, said processing means being arranged to apply a linearity correction to the digital signals; and
wherein the analogue-to-digital conversion means is arranged to operate by oversampling the amplified outputs; and
wherein the analogue-to-digital conversion means is arranged to sample optical path difference intervals corresponding to half a laser fringe.

10. A circuit according to claim 9, wherein each detector is operated in a constant voltage mode.

11. A circuit according to claim 10, wherein each amplifying means includes a preamplifier associated with each detector and the amplifier outputs are combined to provide positive feedback.

12. A circuit according to claim 9, wherein the processing means is arranged to apply a linearity correction according to the following algorithm $$y'=y/(1-\alpha y)$$

where y is the output of the analogue-to-digital converter, y' is the corrected output, and α is a parameter.

13. A circuit according to claim 12, wherein the parameter α is a constant.

14. A circuit according to claim 12, wherein the parameter α is a function of energy incident on the detectors.

15. An infrared microscope including a circuit according to claim 9, further comprising:
a circuit having amplifying means for amplifying the outputs of a detector;
analogue-to-digital conversion means for digitizing the amplified outputs; and
processing means for processing the digitized signals, said processing means being arranged to apply linearity correction to the digital signals.

16. A circuit for processing the outputs of an array of photoconductive detectors, the circuit comprising:
amplifying means for amplifying the outputs of the detectors;
analogue-to-digital conversion means for digitizing the amplified outputs; and
processing means for processing the digitized signals;
said processing means being arranged to apply a linearity correction to the digital signals according to the following algorithm $$y'=y/(1-\alpha y)$$

where y is the output of the analogue-to-digital converter, y' is the corrected output, and α is a parameter.

17. A circuit according to claim 16, wherein the parameter α is a constant.

18. A circuit according to claim 16, wherein the parameter α is a function of energy incident on the detectors.

19. A circuit according to claim 16, wherein each detector is operated in a constant voltage mode.

20. A circuit according to claim 19, wherein each amplifying means includes a preamplifier associated with each detector and the amplifier outputs are combined to provide positive feedback.

21. A circuit according to claim 16, wherein the analogue-to-digital conversion means is arranged to operate by oversampling the amplified outputs.

22. A circuit according to claim 21, wherein the analogue-to-digital conversion means is arranged to sample optical path difference intervals corresponding to half a laser fringe.

23. An infrared microscope including a circuit according to claim 16, further comprising:
   a circuit having amplifier means for amplifying the output of a detector;
   analogue-to-digital conversion means for digitizing the amplified outputs; and
   processing means for processing the digitized signals, said processing means being arranged to apply a linearity correction to the digital signals.

24. A method of processing the outputs of an array of photoconductive detectors, the method comprising:
   amplifying the outputs of the detectors;
   reducing cross talk between the outputs of the array of photoconductive detectors by positive feedback;
   digitizing the amplified outputs; and
   applying a linearity correction to the digitizing the amplified outputs signals.

25. The method as set forth in claim 24 wherein reducing cross talk comprises:
   combining the amplified outputs;
   directing the combined amplified outputs in a positive feedback loop.

26. The method as set forth in claim 24 applying a linearity correction comprises applying a linearity correction according to the algorithm $$y'=y/(1-\alpha y)$$

where y is the output of the analogue-to-digital converter, y' is the corrected output, and $\alpha$ is a parameter.

27. The method as set forth in claim 26, wherein the parameter $\alpha$ is a constant.

28. The method as set forth in claim 26, wherein the parameter $\alpha$ is a function of energy incident upon a detector.

29. The method as set forth in claim 24, further comprising operating a detector in a constant voltage mode.

* * * * *